United States Patent
Levine et al.

(10) Patent No.: US 7,130,686 B1
(45) Date of Patent: Oct. 31, 2006

(54) SELECTION OF PREVENTATIVE ARRHYTHMIA THERAPY BASED ON PATIENT SPECIFIC HISTOGRAM DATA

(75) Inventors: Paul A. Levine, Santa Clarita, CA (US); Gene A. Bornzin, Simi Valley, CA (US); Anne M. Pianca, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 666 days.

(21) Appl. No.: 10/187,501

(22) Filed: Jul. 1, 2002

(51) Int. Cl.
*A61N 1/365* (2006.01)

(52) U.S. Cl. ............................ 607/15; 607/18; 607/19; 607/25; 607/26

(58) Field of Classification Search ................ 607/4–5, 607/9, 14, 15, 17–26
See application file for complete search history.

(56) References Cited

U.S. PATENT DOCUMENTS

| | | |
|---|---|---|
| 5,431,685 A | 7/1995 | Alt |
| 5,458,622 A | 10/1995 | Alt |
| 5,476,483 A | 12/1995 | Bornzin et al. |
| 5,630,834 A | 5/1997 | Bardy |
| 5,733,312 A | 3/1998 | Schloss et al. |
| 5,902,250 A | 5/1999 | Verrier et al. |
| 5,951,593 A * | 9/1999 | Lu et al. ............... 607/14 |
| 6,058,328 A | 5/2000 | Levine et al. |
| 6,080,187 A | 6/2000 | Alt et al. |
| 6,128,534 A | 10/2000 | Park et al. |
| 6,370,431 B1 * | 4/2002 | Stoop et al. ............ 607/14 |
| 2003/0153955 A1 * | 8/2003 | Park et al. .............. 607/17 |

* cited by examiner

*Primary Examiner*—Robert E. Pezzuto
*Assistant Examiner*—Kristen Mullen

(57) ABSTRACT

Methods and systems for providing cardiac therapy are described. In some embodiments, methods and systems are configured to deliver atrial tachyarrhythmia therapy by confirming that a patient is asleep and thereafter administering the therapy. Sleep can be confirmed, in some embodiments, through the use of a histogram that can be calculated using one or more parameters that are monitored by an implantable stimulation device. Parameters can include both physiological and non-physiological parameters. In other embodiments, atrial tachyarrhythmia therapy is delivered by determining desirable times to administer such therapy. Other various systems and methods for administering cardiac therapy are described.

9 Claims, 11 Drawing Sheets

SELECTION OF PREVENTATIVE ARRHYTHMIA THERAPY BASED ON PATIENT SPECIFIC HISTOGRAM DATA

TECHNICAL FIELD

The present invention generally relates to methods and systems for providing cardiac therapy. More particularly, aspects of the invention concern methods and systems for providing cardiac therapies involving controlled delivery of electrical stimulations to a heart for treatment of arrhythmias.

BACKGROUND

Cardiac arrhythmias can generally be thought of as disturbances of the normal rhythm of the heart muscle. Cardiac arrhythmias are broadly divided into two major categories, bradyarrhythmia and tachyarrhythmia. Tachyarrhythmia can be broadly defined as an abnormally rapid heart (e.g., over 100 beats/minute, at rest), and bradyarrhythmia can be broadly defined as an abnormally slow heart (e.g., less than 50 beats/minute). Tachyarrhythmias are further subdivided into two major sub-categories, namely, tachycardia and fibrillation. Tachycardia is a condition in which the electrical activity and rhythms of the heart are rapid, but organized. Fibrillation is a condition in which the electrical activity and rhythm of the heart are rapid, chaotic, and disorganized. Tachycardia and fibrillation are further classified according to their location within the heart, namely, either atrial or ventricular.

In general, atrial arrhythmias are non-life threatening, chronic conditions, because the atria (upper chambers of the heart) are only responsible for aiding the movement of blood into the ventricles (lower chambers of the heart), whereas ventricular arrhythmias are life-threatening, acute events, because the heart's ability to pump blood to the rest of the body is impaired if the ventricles become arrhythmic.

Current treatments for atrial fibrillation include drug, external cardioversion, ablation, and pacing therapy. Each of these treatments has positive and negative aspects. For example, often times side effects associated with drug therapy can lead to low compliance among the patient population. Additionally, most times a patient can be converted to normal sinus rhythm using external cardioversion. However, many times the patients tend to revert back to atrial fibrillation. This can also be the case with ablation therapy. Pacing therapy is currently being clinically investigated to ascertain its applicability as a valid therapy for atrial fibrillation. There are subsets of patients in whom pacing therapy is effective in preventing or reducing the incidence of paroxysmal atrial fibrillation and/or stabilizing the rhythm after pharmacologic therapy or cardioversion has been successful in terminating an episode of persistent atrial fibrillation.

Internal cardioversion is yet another option for treating atrial tachyarrhythmias such as atrial fibrillation. This option has an advantage in that most times cardioversion is successful, and hospitalization (outpatient and inpatient) is not required. There are existing devices for treating atrial fibrillation using internal cardioversion. In one instance, a patient activates a device to provide shock therapy by simply placing a credit card-like activator over an implanted device. The disadvantage of this type of therapy delivery is that it is patient dependent. In many cases patients who receive uncomfortable shocks are less likely to deliver therapy to themselves since they perceive the pain from the shock to be worse than the side effects of atrial fibrillation.

Other devices can be programmed to provide shocks during a certain times of the day. For example, the device might be programmed to administer therapy to a patient suffering from atrial fibrillation early in the morning when the patient desires to wake up.

Atrial fibrillation is a disease that affects many active people who lead busy lives and often cover several time zones each week, and in some cases each day. For these types of people, their desired "wake-up" time can vary by 6 hours or more within a given time zone. However, programming a device to administer therapy at the same time during a day (e.g. in the early morning waking hours) is not ideal for a patient who changes time zones or whose lifestyle habits are highly variable.

This invention arose out of concerns associated with providing improved methods and systems for administering cardiac therapy to patients, and particularly, to patients who suffer from atrial fibrillation.

SUMMARY

Methods and systems for providing cardiac therapy are described. In some embodiments, methods and systems are configured to deliver atrial tachyarrhythmia therapy by confirming that a patient is asleep and thereafter administering the therapy. Sleep can be confirmed, in some embodiments, through the use of a histogram that can be calculated using one or more parameters that are monitored by an implantable stimulation device. Parameters can include both physiological and non-physiological parameters. In one particular embodiment, the patient's activity variance, as measured by the stimulation device, serves as the basis upon which a histogram is built.

In other embodiments, atrial tachyarrhythmia therapy is delivered by determining desirable times to administer such therapy. Desirable times can be determined using some of the same histogram principles mentioned above.

Yet other embodiments employ the use of various thresholds, in connection with the described histogram approach, to ensure that a patient's current state corresponds to a portion of the histogram that is desirable for administering therapy.

In another embodiment, atrial tachyarrhythmia therapy can be administered from both an automatic mode that is designed to administer the therapy as a function of the patient's state or time of day, as well as a patient-selectable mode that allows a patient to initiate the fibrillation therapy themselves.

Other embodiments provide methods and systems that select preventative or treatment therapies based on either the time of day or a patient's state.

BRIEF DESCRIPTION OF THE DRAWINGS

Further features and advantages of the claimed embodiments can be more readily understood by reference to the following description taken in conjunction with the accompanying drawings, in which:

DETAILED DESCRIPTION

The following description is of the best mode presently contemplated for practicing the described embodiments. This description is not to be taken in a limiting sense, but rather is made merely for the purpose of describing the general principles of the inventive embodiments. The scope of the described embodiments should be ascertained with reference to the issued claims. In the description of the embodiments that follow, like numerals or reference designators will be used to refer to like parts or elements throughout.

Overview

Methods and systems for providing cardiac therapy are described. In some embodiments described below, the cardiac therapy comprises atrial tachyarrhythmia therapy, and various methods and systems are configured to deliver atrial tachyarrhythmia therapy by confirming that a patient is asleep and, thereafter, administering the therapy. Sleep can be confirmed, in some embodiments, through the use of a histogram onboard an implantable stimulation device. The histogram can be calculated by the stimulation device using one or more parameters that are monitored by the device. Parameters can include both physiological and non-physiological parameters. In one particular embodiment, the patient's activity variance, as measured by the stimulation device, serves as the basis upon which a histogram is built. In other embodiments, atrial tachyarrhythmia therapy is delivered by determining desirable times to administer such therapy. Desirable times can be determined using some of the same histogram principles mentioned above and described in detail below. Yet other embodiments employ the use of various thresholds, in connection with the described histogram approach, to ensure that a patient's current state corresponds to a portion of the histogram that is desirable for administering therapy. In yet other embodiments, atrial tachyarrhythmia therapy can be administered from both an automatic mode that is designed to administer the therapy as a function of the patient's state or time of day, as well as a patient-selectable mode that allows a patient to initiate the fibrillation therapy themselves.

Other embodiments provide a collection of robust methods and systems that select preventative or treatment therapies based on either the time of day or a patient's state.

Exemplary Stimulation Device

The techniques that are described below are intended to be implemented in connection with a stimulation device that is configured or configurable to stimulate or shock a patient's heart.

Figure 1:
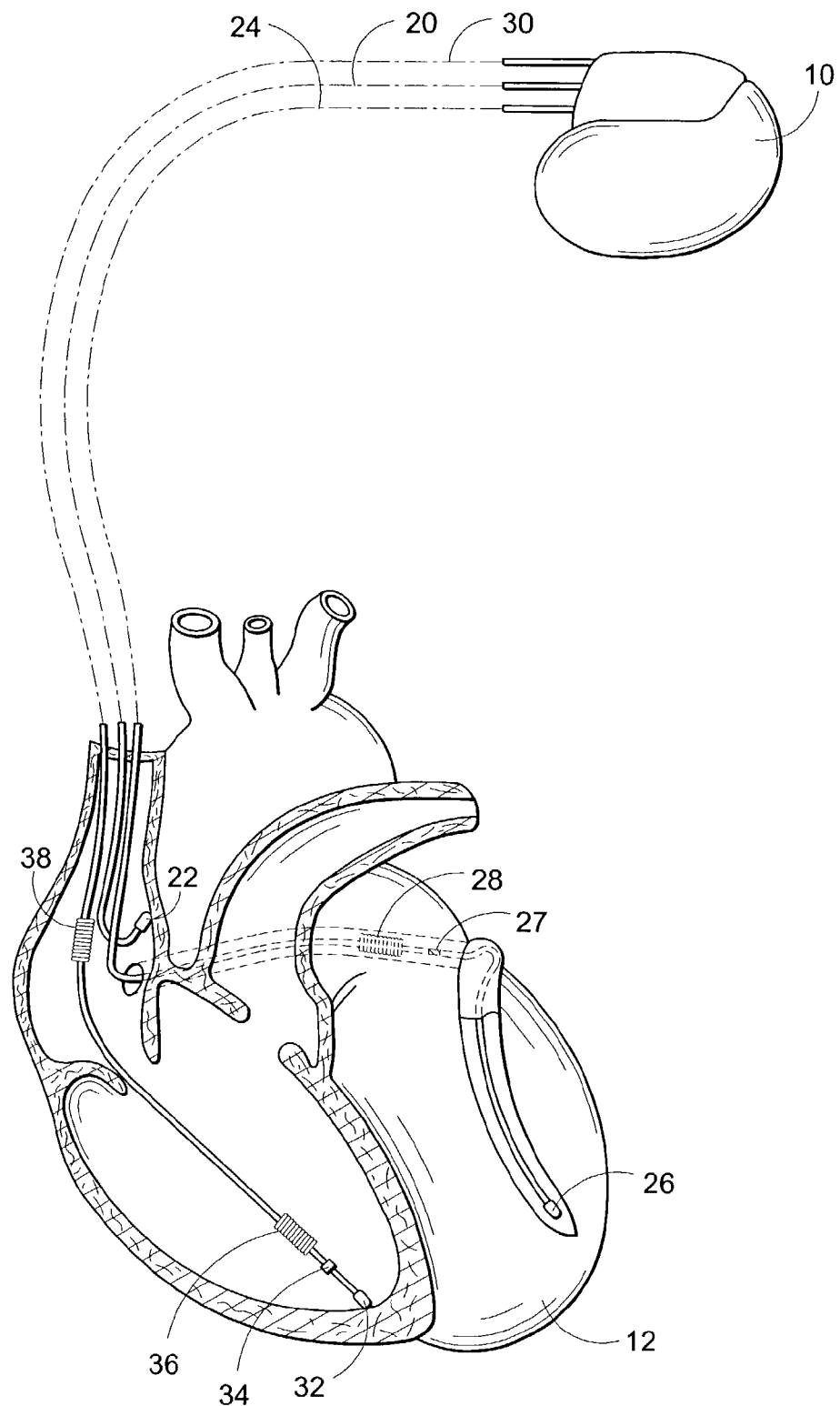
FIG. 1 is a simplified diagram illustrating an implantable stimulation device in electrical communication with leads implanted into a patient's heart for delivering multi-chamber stimulation and shock therapy.

FIG. 1 shows an exemplary stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

Stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
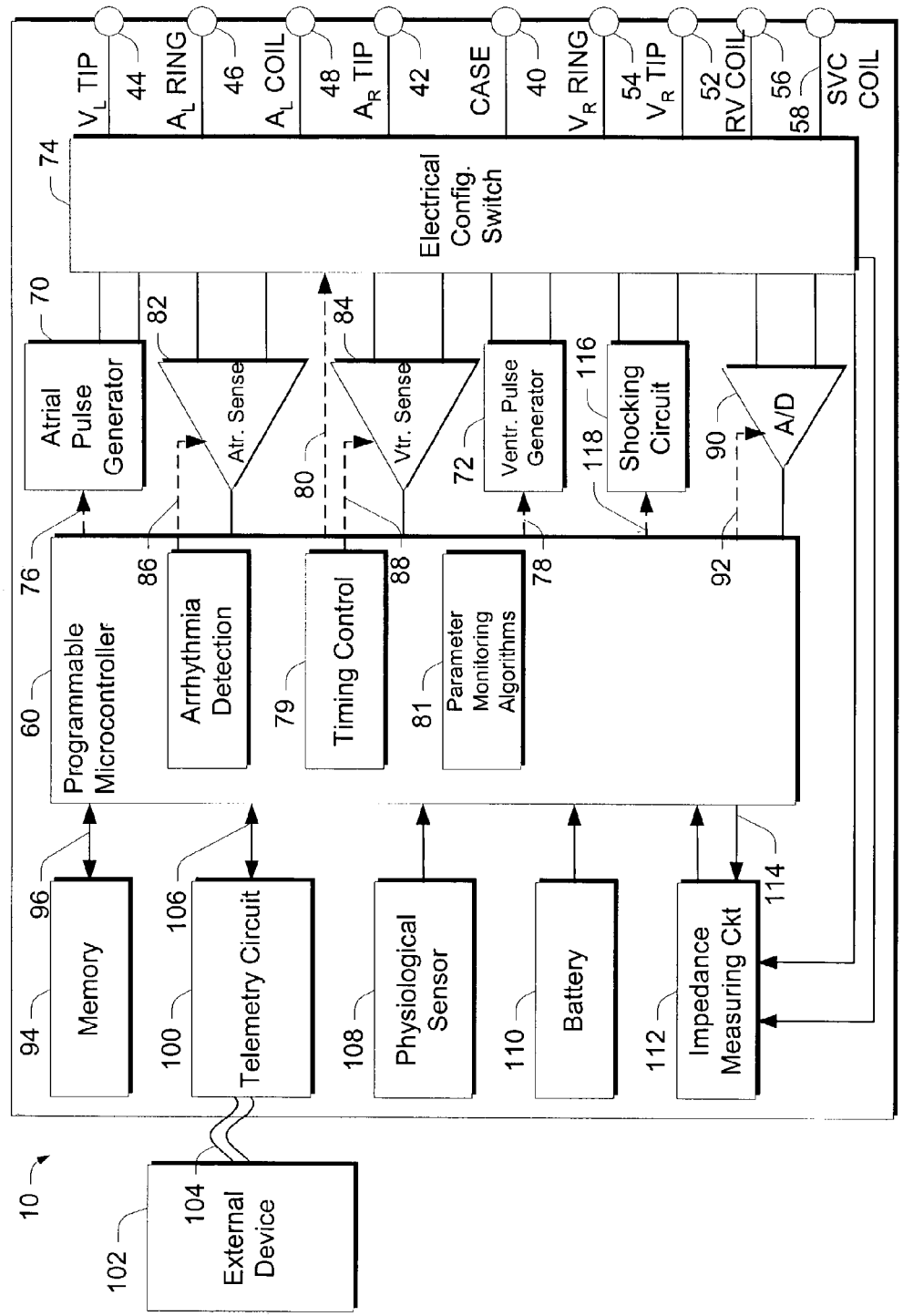
FIG. 2 is a functional block diagram of a multi-chamber implantable stimulation device illustrating the basic elements of a stimulation device which can provide cardioversion, defibrillation and pacing stimulation in four chambers of the heart.

FIG. 2 shows an exemplary, simplified block diagram depicting various components of stimulation device 10. The stimulation device can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the inventive techniques and methods described below can be implemented in connection with any suitably configured or configurable stimulation device. Accordingly, one of skill in the art could readily duplicate, eliminate or disable the appropriate circuitry in any desired combination to provide a device capable of treating the appropriate chamber(s) with cardioversion, defibrillation and pacing stimulation.

Housing 40 for stimulation device 10 is often referred to as the "can", "case" or "case electrode", and may be programmably selected to act as the return electrode for all "unipolar" modes. Housing 40 may further be used as a return electrode alone or in combination with one or more of the coil electrodes 28, 36 and 38, for shocking purposes.

Housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design and operation of the microcontroller 60 are not critical to the described embodiments. Rather, any suitable microcontroller 60 may be used that carries out the functions described herein. The use of microprocessor-based control circuits for performing timing and data analysis functions are well known in the art.

FIG. 2 also shows an atrial pulse generator 70 and a ventricular pulse generator 72 which generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

Microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

Microcontroller 60 further includes one or more parameter monitoring algorithms 81 that can be utilized by the stimulation device 10 for determining desirable times to administer atrial tachyarrhythmia therapy, as will become more apparent below.

A switch 74 includes a plurality of switches for connecting the desired electrodes to the appropriate I/O circuits, thereby providing complete electrode programmability. Accordingly, switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. A capture threshold search can desirably be performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. One feature of the described embodiments is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 can further include a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the described embodiments and is shown only for completeness.

The described embodiments can utilize a "sleep state" or diurnal sensor that can detect sleep and wake states. One such sensor is known as "activity variance" wherein an activity sensor is monitored diurnally to detect the low variance in the measurement corresponding to the sleep state. As used herein, "sleep state" refers to a condition that generally indicates that a patient is asleep.

For a complete description of the activity variance sensor, see U.S. Pat. No. 5,476,483 (Bornzin et. al), issued Dec. 19, 1995, which patent is hereby incorporated by reference.

The stimulation device additionally includes a battery 110 that provides operating power to all of the circuits shown in FIG. 2. For the stimulation device 10, which employs shocking therapy, the battery 110 is capable of operating at low current drains for long periods of time (e.g. preferably less than 10 μA), and is capable of providing high-current pulses (for capacitor charging) when the patient requires a shock pulse (e.g. preferably, in excess of 2 A, at voltages above 2 V, for periods of 10 milliseconds or more). The battery 110 also desirably has a predictable discharge characteristic so that elective replacement time can be detected. Accordingly, the device 10 preferably employs a power source sufficient to deliver the high voltage shock therapy. One such example is the lithium/silver vanadium oxide battery, as is true for most (if not all) current devices capable of delivering high voltage therapy.

The stimulation device 10 can further include magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

FIG. 2 also shows an impedance measuring circuit 112 which is enabled by the microcontroller 60 via a control signal 114. The known uses for an impedance measuring circuit 120 include, but are not limited to, lead impedance surveillance during the acute and chronic phases for mechanical integrity of the lead, measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where the stimulation device 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of an organized tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of ventricular fibrillation which is a very disorganized rapid ventricular arrhythmia. Accordingly, the microcontroller 60 is capable of controlling the synchronous or asynchronous delivery of the shocking pulses.

Figure 3:
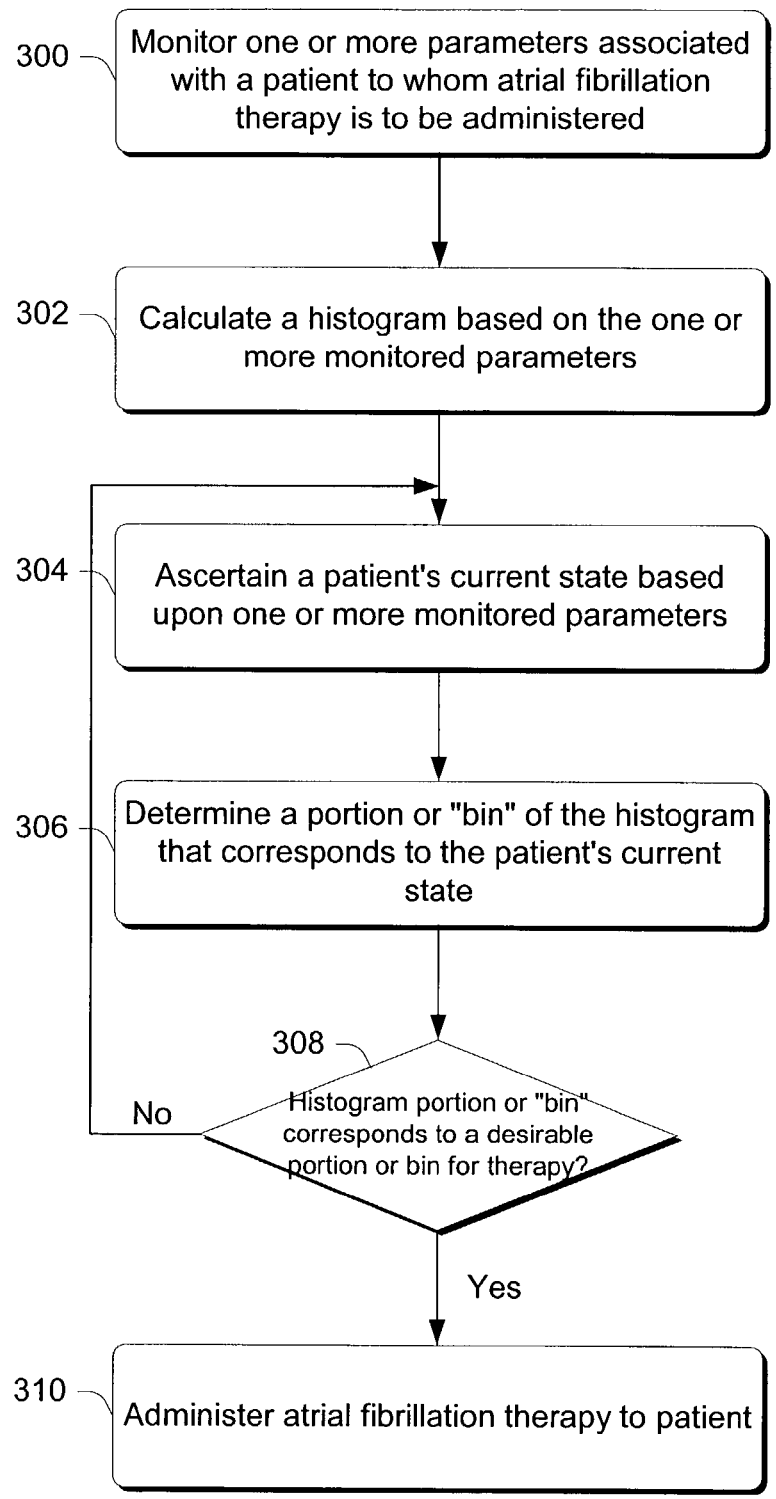
FIG. 3 is a flow diagram that describes steps in a method in accordance with one embodiment.

Using a Patient-Specific Histogram to Determine when to Administer Atrial Tachyarrhythmia Therapy FIG. 3 shows an exemplary flow diagram that describes steps in a method in accordance with one described embodiment. The method can be implemented in connection with any suitably configured stimulation device. One specific and non-limiting example of a stimulation device was given above.

In this flow diagram, and the other flow diagrams described herein, various algorithmic steps are summarized in individual "blocks". Such blocks describe specific actions or decisions that are made or carried out as an algorithm proceeds. Where a microcontroller (or equivalent) is employed, the flow charts presented herein provide a basis for a "control program" or software that may be used by such a microcontroller (or equivalent) to effectuate the desired control of the stimulation device. Those skilled in the art may readily write such a control program based on the flow charts and other descriptions presented herein. It is to be understood and appreciated that the inventive subject matter described herein includes not only stimulation devices when programmed to perform the steps described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

Before a description of the FIG. 3 flow diagram is given, consider the following. With respect to delivering atrial tachyarrhythmia therapy, it is generally desirable and in many instances advantageous to perform such therapy at certain times relative to each patient. These times may be different from patient to patient. For example, times during which a patient is in a profound state of rest or sleep are viewed as very desirable for reasons that include minimizing the discomfort perceived by the patient and/or the risk that the patient may present to himself or others while undergoing treatment. There may be additional times, different from times of profound rest or sleep, where it can be desirable to deliver atrial tachyarrhythmia therapy. For example, some patients may desire for therapy administration during their early waking hours as part of the waking process.

In accordance with the embodiment about to be described, a stimulation device is programmed so that it uses a patient-specific histogram to effect administration of atrial tachyarrhythmia therapy. Use of a patient-specific histogram is advantageous because it can allow the stimulation device to accurately determine when a particular patient is to receive their atrial tachyarrhythmia therapy.

Step 300 monitors one or more parameters associated with a patient to whom atrial tachyarrhythmia therapy is to be administered. In the discussion that follows, it should be assumed that the patient has been detected to have an atrial tachyarrhythmia such as atrial fibrillation, although that step is not explicitly shown in the drawings. Step 302 calculates a histogram based on the monitored parameter(s). As will be appreciated by those of skill in the art, a histogram is a specialized graph or plot used in statistics. In its most common form, an independent variable is plotted along a horizontal axis, and a dependent variable (usually a percentage) is plotted along a vertical axis. The independent variable can typically attain only a finite number of discrete values rather than a continuous range of values. The dependent variable can span a continuous range.

The monitored parameters can be any suitable parameters for which a histogram can be constructed and used to determine when to administer atrial tachyarrhythmia therapy. Specific examples of monitoring various patient-associated parameters are described in U.S. Pat. Nos. 6,128,534 and 5,733,312, the disclosures of which are incorporated by reference herein. For example, in some embodiments, it is desirable to administer atrial tachyarrhythmia therapy when a patient is in a profound state of rest or sleep. In these instances it is desirable to monitor diurnally-varying parameters. Diurnally-varying parameters are parameters that change detectably based upon whether a patient is awake or asleep. These parameters can be physiological parameters or non-physiological parameters.

Examples of physiological parameters can include, without limitation, QT-interval and ventricular gradient, which are both derived from the cardiac signal itself and are associated with contractility. Specifically, when a patient is asleep, their heart rate slows down and accordingly, the QT-interval prolongs. The prolongation of the QT-interval can be measured and can indicate when a patient is asleep. Other physiological parameters can include tidal volume, minute ventilation (which is a combination of respiration and tidal volume), respiration rate, intrinsic heart rate, oxygen saturation, blood pressure, paced depolarization integral (PDI), the derivative of an evoked response waveform, amplitude of the evoked response, duration of the evoked response, stroke volume, and the like, to name just a few.

Examples of non-physiological parameters can include, without limitation, the activity of the patient. Specifically, when a patient is asleep they are less active than when they are awake. Sensors can detect patient activity from which an activity variance can be ascertained and form the basis of a histogram. An exemplary approach is described in U.S. Pat. No. 5,476,483, assigned to the assignee of this document and incorporated by reference.

Figure 4:
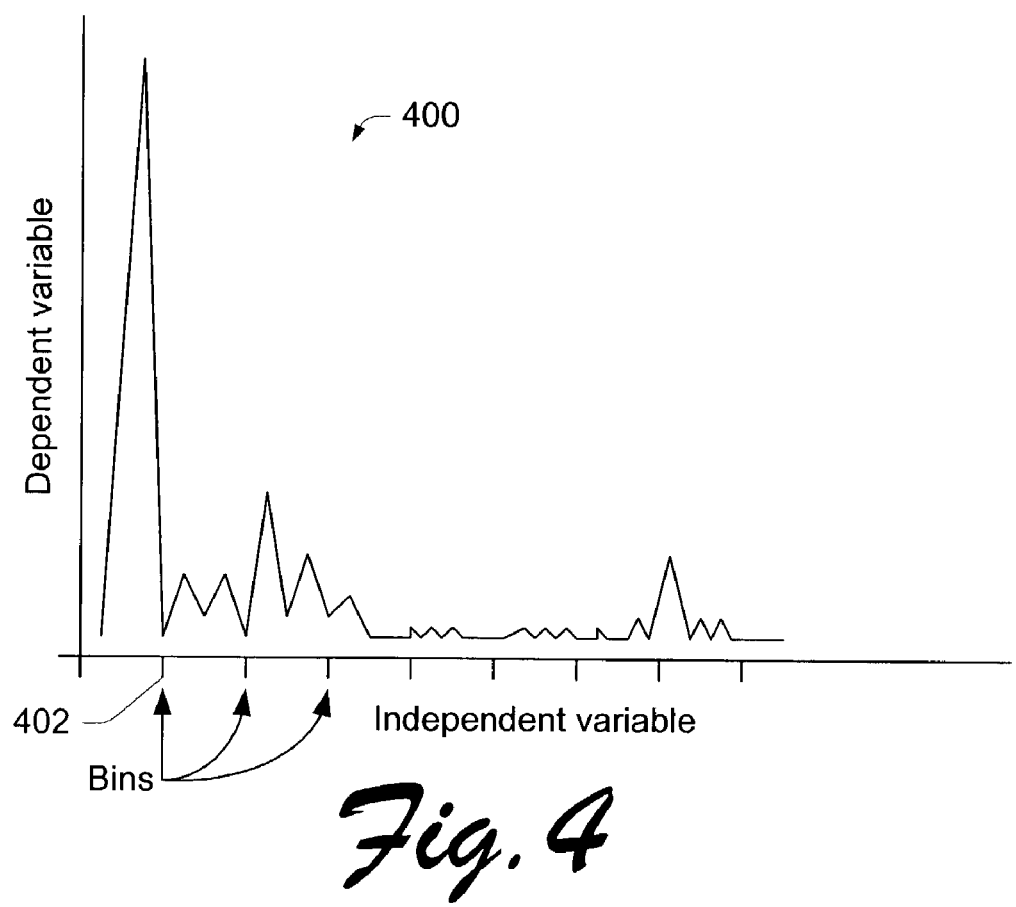
FIG. 4 is a simplified diagram of a histogram that is useful in understanding some embodiments.

In accordance with the described embodiment, the calculated histogram contains a number of "bins" that are associated with values of the independent variable. For example, FIG. 4 shows a very simplified histogram at 400. The independent variable is plotted on the x axis and the dependent variable is plotted on the y axis. A number of bins are shown along the x axis and can be associated with various patient states. Specifically, consider the case where a patient's activity or activity variance is used as the basis for the histogram. (See, e.g. U.S. Pat. No. 5,476,483, incorporated by reference above). In that case, an independent variable can comprise the activity variance or count which is computed as a function of the patient's activity. The dependent variable can comprise the normalized number of events. Once the histogram is calculated, each bin can be associated with a particular state of the patient. For example, in the FIG. 4 histogram, a bin 402 is shown and corresponds to the highest bin of the activity variance histogram that contains activity variance measurements that were derived while the patient was sleeping. Thus, everything below bin 402 in the histogram corresponds to activity variance measurements that were taken while the patient was, in fact, asleep.

Continuing, step 304 ascertains or confirms a patient's current state based upon one or more monitored parameters. These parameters can be both physiological and/or non-physiological parameters and can be ascertained from sensors carried on the stimulation device. This step is desirably performed when a patient is determined to be experiencing an atrial tachyarrhythmia such as atrial fibrillation, and is directed to identifying an appropriate time to administer atrial tachyarrhythmia therapy. Step 306 determines a portion or "bin(s)" of the histogram that correspond to the patient's current state. Step 308 then determines whether the histogram portion or "bin(s)" correspond to a desirable portion or bin for therapy. For example, if a patient's monitored parameters places them in a bin associated with sleep, and they are experiencing atrial fibrillation, then step 310 can administer atrial tachyarrhythmia therapy to the patient. Any suitable atrial tachyarrhythmia therapy can be delivered to the patient, with examples being given above.

If, on the other hand, the histogram portion or bin in which a patient's state places them is not desirable for atrial tachyarrhythmia therapy (e.g. the patient might be active in the middle of the day), then the method branches back to step 304 and continues to monitor the patient's state until such a time when therapy can be administered.

Use of a histogram in the context of delivering atrial tachyarrhythmia therapy is a particularly powerful tool, as the histogram serves to define accurate markers that are associated with patient states. These accurate markers can remove any uncertainty with respect to the patient's present state. That is, a histogram based on the above-described physiological or non-physiological parameters can accurately describe various patient states so that atrial tachyarrhythmia therapy can be administered with much more precision with regard to a patient's comfort. For example, if a patient desires to receive atrial defibrillation therapy only during times when they are in fact asleep, the above-described histogram approach can be used to ensure or confirm that the patient is in fact asleep.

The described histogram approach is advantageous in that it overcomes many of the shortcomings of previous approaches. Specifically, the described approach does not necessarily rely on, and can be independent of time measurements provided by an external clock or timer. For example, administration of therapy does not need to be tied to any one particular time of day such as early morning when a patient may be likely, but not guaranteed to be asleep. Additionally, the described approach can be independent of time zones or a patient's movement through and adjustment to different time zones. Thus, a patient may more freely travel about without worrying about the impact that their movement may have on their atrial tachyarrhythmia therapy. For example, if a stimulation device were programmed to administer any needed atrial tachyarrhythmia therapy at 2 A.M. in the morning for a patient living in Seattle, and the patient travels to visit relatives in Pennsylvania, the stimulation device would now be effectively programmed to deliver therapy at 5 A.M. local time. This could be problematic particularly if the patient is an early riser and desires to be treated during sleep. Additionally, the described approach can be independent of the position of the patient as indicated by any position sensors.

Patient-Specific Histograms with Thresholds

As noted above, the use of a histogram advantageously enables atrial tachyarrhythmia therapy to be administered with precision with respect to various patient states that are desirable states for treatment. There are additional instances when the histogram can be used to even more precisely select the appropriate times for therapy administration. For example, consider the situation where a physician desires to administer atrial tachyarrhythmia therapy not only when a patient is asleep, but when the patient is in a deep state of sleep. In this case, the histogram can be used to ascertain or confirm that a patient's current state corresponds to a bin associated with sleep. Further, one or more thresholds can be set to ensure that the patient is in a state that corresponds to a sleep bin for a definable amount of time, thus ensuring a deep state of sleep.

Figure 5:
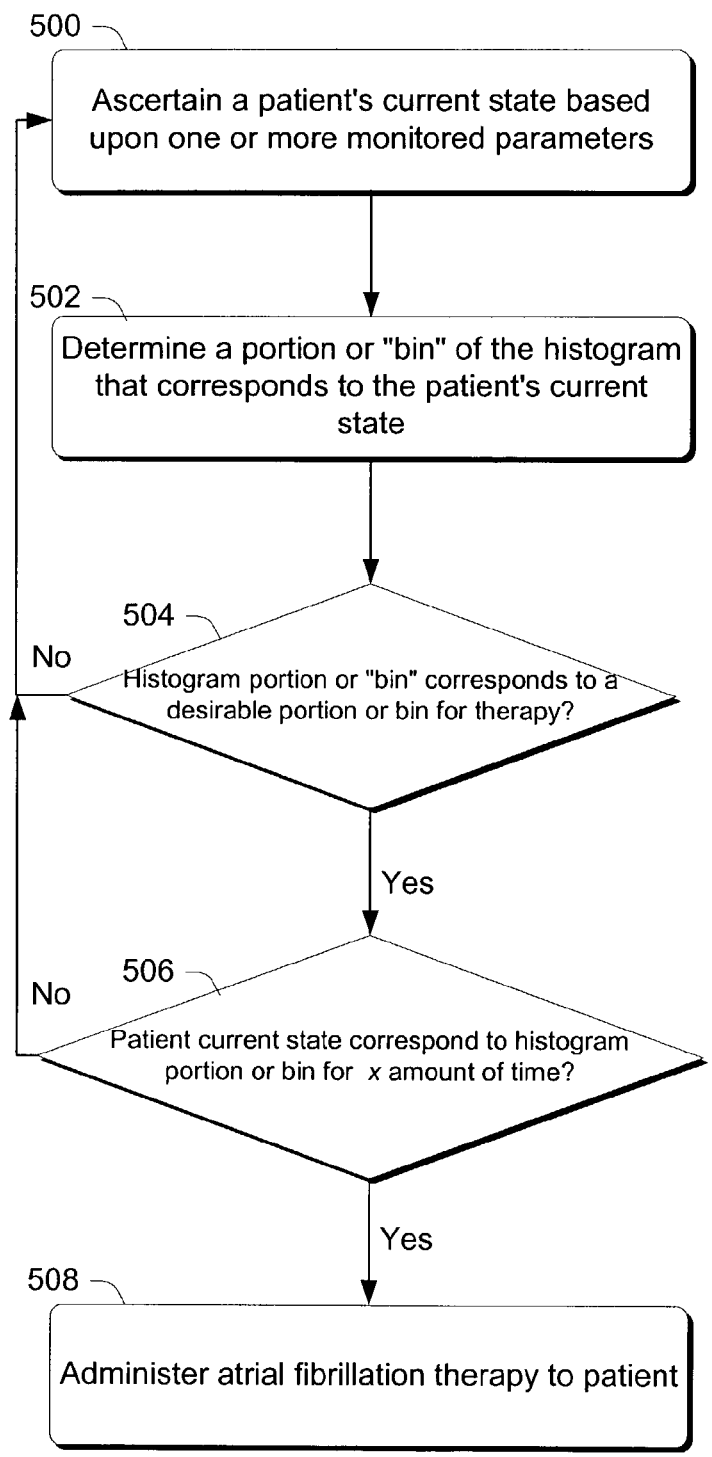
FIG. 5 is a flow diagram that describes steps in a method in accordance with one embodiment.

FIG. 5 shows an exemplary flow diagram that describes steps in a method in accordance with one described embodiment. The method can be implemented in connection with any suitably configured stimulation device. One specific and non-limiting example of a stimulation device was given above.

In the method about to be described, it is assumed that the histogram has already been calculated based upon one or more of the patient's monitored parameters (steps 300 and 302 in FIG. 3).

Step 500 ascertains a patient's current state based upon one or more monitored parameters. This step can be implemented as described above. Step 502 determines a portion or bin of the histogram that corresponds to the patient's current state. Step 504 then determines whether the histogram portion or bin corresponds to a desirable portion or bin for therapy. If not, the method branches back to step 500. If so, step 506 determines if the patient's current state corresponds to the histogram portion or bin for a determinable or definable amount or period of time. If not, the method returns to step 500. If so, step 508 administers atrial tachyarrhythmia therapy to the patient.

Consider the following example. A patient falls asleep and is slated for atrial fibrillation treatment once they are determined to be in a state that corresponds to a sleep bin of the histogram. Assume, however, that the patient wakes up at 1 A.M. to get a glass of water and returns to bed and has just fallen asleep. It is possible that, without a threshold time requirement, a patient might be given atrial tachyarrhythmia therapy as soon as they enter the sleep bin of the histogram. This timing might, however, coincide with a state of light sleep or drowsiness. By using a threshold time to define an amount of time a patient's state should coincide with a particular histogram bin, the physician can be more assured that the patient is in a deep state of sleep when therapy is administered. Exemplary threshold times can be in the range of ½ hour to 2 hours in some embodiments.

Consider further the following. Step 506 can be implemented by defining multiple threshold criteria that are utilized to assess a patient's current state. As an example, consider the following threshold criteria. Step 506 may test a patient's current state to ascertain whether both of the following are true prior to administering atrial tachyarrhythmia therapy: (1) for 80% of the last two hours, has the patient's state been associated only with histogram bins that correspond to a sleep state?; and (2) for 100% of the last 10 minutes has the patient's state been associated with histogram bins that correspond to a sleep state. In this manner, there is an added degree of assurance that a particular patient is, in fact asleep, prior to therapy administration. Thus, in this instance, step 506 can be implemented by defining multiple temporal-based rules each of which are associated with a patient's state, and evaluating each of the rules to ensure that a patient is in a given state prior to therapy administration. In the example above, the rules comprise percentage-based rules that define different percentages of time that a patient's state is associated with a particular histogram-defined bin. As will be appreciated by those of skill in the art, other temporal-based rules are possible.

Confirming Patient State Using Multiple Parameters or Multiple Sensors

There are circumstances when it is desirable to independently confirm that a patient is in a particular state before administering atrial tachyarrhythmia therapy. In these circumstances, the stimulation device can be programmed to use multiple parameters or multiple sensors to determine or confirm a patient state.

Consider the following example. The stimulation device has constructed a histogram based on monitoring a patient's activity as discussed above in connection with FIG. 3. Assume that a patient is experiencing atrial fibrillation and is slated for therapy when they are determined to be in a state that coincides with the histogram's sleep bin or bins. Assume now that the patient is determined to be in a state that coincides with one or more sleep bins, but that a position sensor in the stimulation device indicates that the patient is not prone (as they usually are when they are asleep), but rather is upright. In this example, there appears to be two inconsistent pieces of information—first, the monitored parameters associated with the histogram indicate that the patient is asleep; second, however, a position sensor indicates that the patient is not in their typical sleep position (i.e. prone). Perhaps in this case, the patient has awaken to get a glass of water. In this patient's present state, it is more desirable to wait until the patient is prone and confirmed to be asleep before administering therapy.

Figure 6:
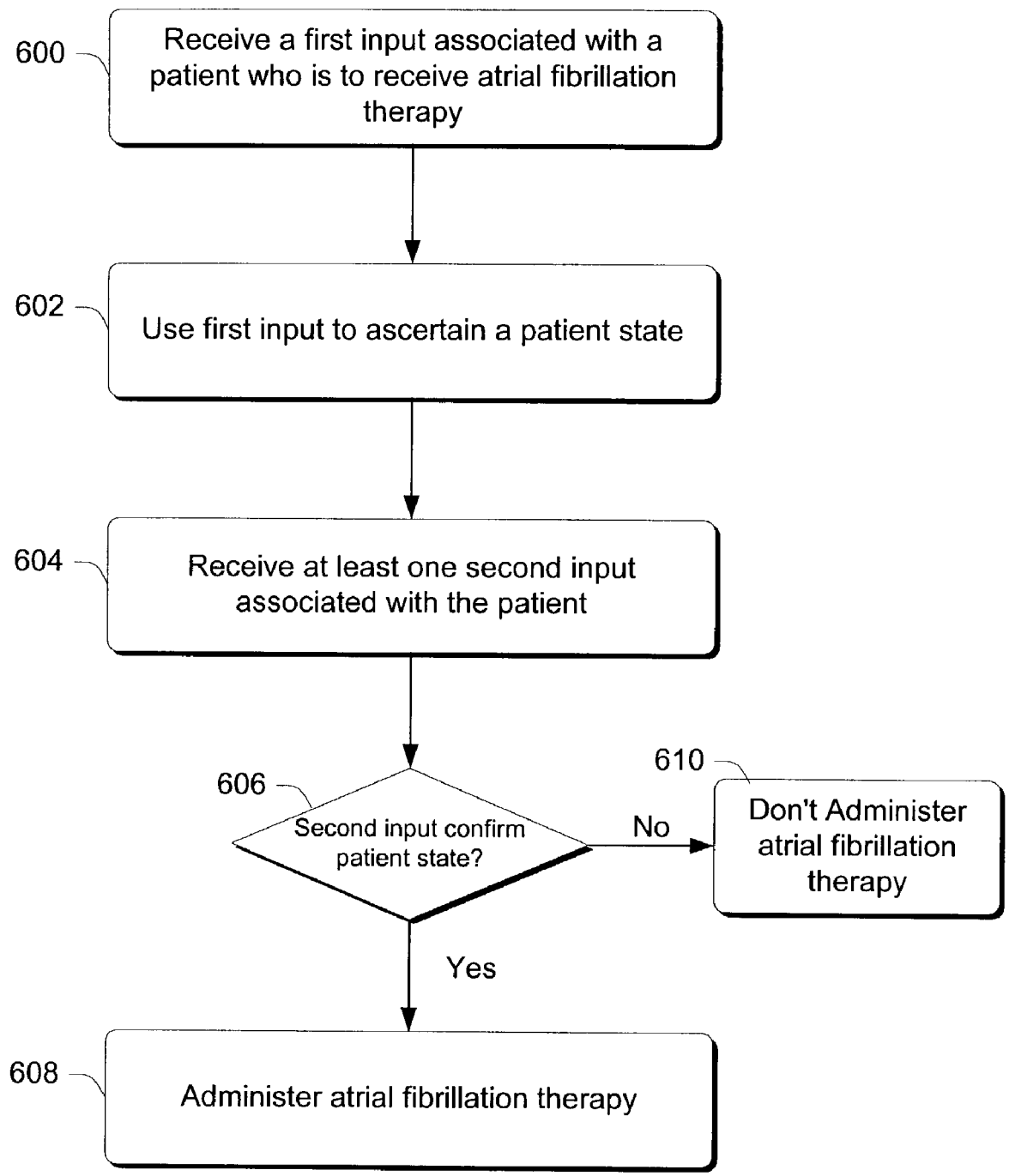
FIG. 6 is a flow diagram that describes steps in a method in accordance with one embodiment.

FIG. 6 shows an exemplary flow diagram that describes steps in a atrial tachyarrhythmia therapy method in accordance with one described embodiment. The method can be implemented in connection with any suitably configured stimulation device. One specific and non-limiting example of a stimulation device was given above.

Step 600 receives a first input associated with a patient who is to receive atrial tachyarrhythmia therapy. This first input can come from any suitable sensor that is associated with the stimulation device. It is to be appreciated and understood that the sensor need not necessarily be one that provides data from which a histogram can be calculated. Suitable sensors can comprise both physiological and non-physiological sensors, examples of which are given above. Step 602 uses the first input to ascertain a patient state that is a desirable state for administering atrial tachyarrhythmia therapy. In one embodiment, the desirable state is the patient's sleep state. For example, if the first input comes from a sensor that senses a patient's physical position (i.e. prone versus upright), then this step would be implemented by the stimulation device ascertaining that a patient was either prone or upright. In one embodiment, the first input can be of the type that is used to ascertain one or more desirable histogram bins that define desirable times to administer atrial tachyarrhythmia therapy.

Step 604 receives at least one second input associated with the patient. This second input can come from the same or a different sensor(s). Step 606 determines whether the second input confirms that patient's state. Consider the case where the first input (step 600) is used to derive an activity variance histogram and the second input is associated with the QT-interval. If, in this case, the patient's state corresponds to a sleep bin of the histogram, and the QT-interval is sufficiently prolonged as to indicate sleep, then step 608 administers atrial tachyarrhythmia therapy. If, on the other hand, the QT-interval is of the type that suggests that the patient is not, in fact, asleep, then step 610 does not administer atrial tachyarrhythmia therapy. It is to be appreciated and understood that step 604 can receive multiple different inputs and use each of the inputs to confirm the patient's state.

Patient-Selectable Atrial Tachyarrhythmia Therapy Option

There can be situations where it is desirable to automatically treat a patient for atrial fibrillation when, for example, the patient is asleep, but yet retain the flexibility to administer therapy sooner if it would be advantageous to do so. Consider the following example. A patient's stimulation device first initially determines that a patient is experiencing atrial fibrillation an hour after the person wakes up in the morning. If the stimulation device waits to administer therapy until sleep is confirmed during the patient's next sleep period, this could mean waiting 19 hours or more to administer therapy. It may, in these situations, be more desirable to treat the patient sooner. Accordingly, in this embodiment, the stimulation device is configured to automatically treat a patient as described above. Additionally, however, the stimulation device is also configured to give the patients the option of initiating atrial tachyarrhythmia therapy themselves.

Figure 7:
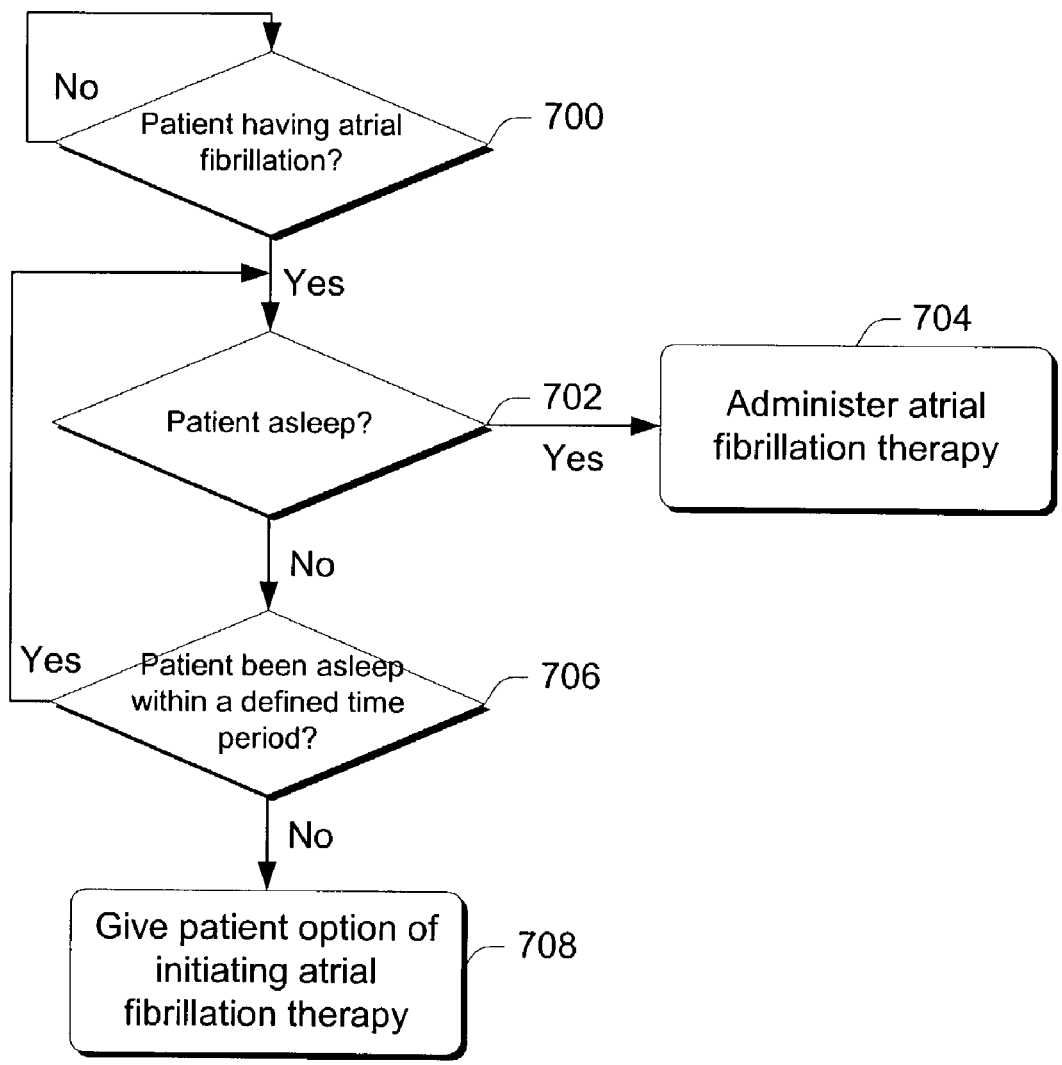
FIG. 7 is a flow diagram that describes steps in a method in accordance with one embodiment.

FIG. 7 shows an exemplary flow diagram that describes steps in a atrial tachyarrhythmia therapy method in accordance with one described embodiment. The method can be implemented in connection with any suitably configured stimulation device. One specific and non-limiting example of a stimulation device was given above.

Step 700 determines whether a patient is experiencing atrial fibrillation. This step can be implemented in any suitable way. If the patient is experiencing atrial fibrillation, step 702 determines whether the patient is asleep. This step can be implemented in any suitable way. For example, exemplary sensors and patient-associated parameters have been discussed above that can be utilized to ascertain whether a patient is asleep. This step can be implemented using any one or any suitable combination of the above techniques and systems. In addition, this step can be implemented using any known techniques or systems that are typically used to determine whether a patient having a stimulation device is asleep. If the patient is determined to be asleep, then step 704 administers atrial therapy. This step can be implemented using known atrial tachyarrhythmia therapy techniques. If, on the other hand, step 702 determines that the patient is not asleep, then step 706 determines whether the patient will be asleep within a defined time period. This time period can be preset or can be programmably changed. For example, a patient's physician may determine that for a particular patient they would prefer to treat the atrial fibrillation no later than four hours after it is first detected. In this case, step 706 would determine whether the patient will be asleep within five hours. This step is implemented by the method branching back to step 702 to ascertain whether and when the patient is, in fact, asleep. Step 706 can be implemented by tracking historical data associated with the patient's sleep cycles and then calculating the time remaining until the patient will enter a time period associated with their historical sleep cycles.

If step 706 determines that a patient will not be asleep within the defined time period, then step 708 gives the patient the option of initiating their atrial tachyarrhythmia therapy. This step can be implemented by generating a notification for the patient. For example, in some instances, the stimulation device can be configured to stimulate a patient's pectoral muscle via a small electrical current that is sufficient to cause a slight but perceptible twitch. When a patient notices this twitch, they can then take steps in initiate their atrial tachyarrhythmia therapy.

At this point, the patient can initiate defibrillation by placing a magnet over the pacemaker to enable atrial defibrillation therapy to be delivered within a few seconds to a few minutes following magnet application. Alternate schemes of patient notification can be utilized. For example, the implanted device can make a beeping sound using a piezoelectric element, or can vibrate using an electromechanical actuator. Other notification options can be used including telemetering a signal to a nearby receiver that can be worn by the patient like a pager or located near their bedside. The receiver can then notify the patient with a message screen or a flashing light, or can transmit the information using a cell phone network. When using a cell phone network, the receiver that has incorporated cell phone technology can call the patient on the patient's home phone using a voice synthesized message. Or, alternately, the receiver can call to a central station that will notify a physician who can then contact the patient. Alternately, the receiver can call a central station that will automatically call the patient on the telephone and notify the patient with a voice message.

Once the patient is notified, the defibrillation can be actuated by the patient, or by the patient's physician using a telemetry device that communicates with the implanted device to trigger defibrillation or, as mentioned earlier, by applying a simple magnet that is easily detected by the implanted device.

Selecting Preventative Therapy or Tiered Therapies Based on Time of Day

Those of skill in the art understand the concept of tiered therapies. Tiered therapies are essentially different therapies that can be categorized in terms of their aggressiveness. For example, when a patient is treated with tiered therapies, they are typically started with a less aggressive therapy and moved gradually to a more aggressive therapy if the less aggressive therapy fails to achieve the desired result. Examples of tiered therapies are given above.

In some instances, it is desirable to provide preventative therapy to a patient who has not yet incurred a condition that requires treatment. Consider for example dynamic atrial overdrive or DAO. In DAO, the stimulation device might set a base rate of 60 bpm. Upon detecting two P-waves, the base rate is increased by some programmable amount—e.g. from 60 bpm to 70 bpm. Now, the new base rate is utilized for some programmable duration (e.g. 16 to 32 beats)—and then it slowly starts to decrease back down to the original base rate of 60 bpm. The aggressiveness of the increase or "bounce up" is likely more important during the day when a person is more active or has more variability to their heart rate, than at night when a person is less active and has less variability to their heart rate. For example, during the day, a bounce up of 10 bpm might be used, whereas at night a bounce up of only 5 bpm might be used.

In accordance with this embodiment, different therapies can be selected or adjusted based on the time of day.

Figure 8:
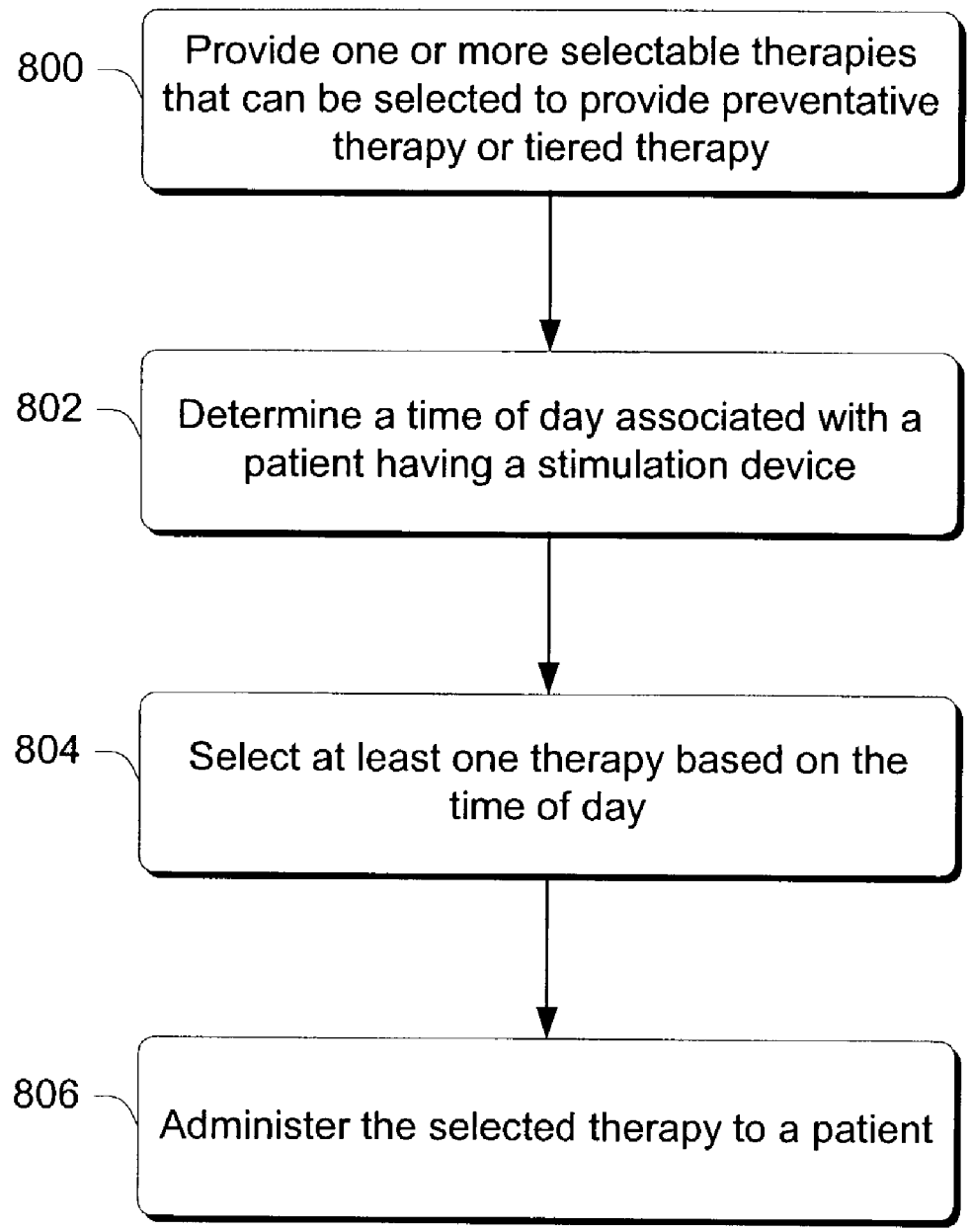
FIG. 8 is a flow diagram that describes steps in a method in accordance with one embodiment.

FIG. 8 shows an exemplary flow diagram that describes steps in a therapy method in accordance with one described embodiment. The method can be implemented in connection with any suitably configured stimulation device. One specific and non-limiting example of a stimulation device was given above.

Step 800 provides one or more selectable therapies that can be selected to provide preventative therapy or tiered therapy. Any suitable therapies can be provided and are typically provided by programming the stimulation device to provide such therapies. Step 802 determines a time of day associated with a patient having a stimulation device. This step can be implemented in any suitable way. For example, the stimulation device can have an internal clock that it uses to ascertain the time of day. Step 804 selects at least one preventative therapy based on the time of day. In the example above, this step is implemented by adjusting a parameter associated with a particular therapy-DAO. This step can also be implemented by selecting one therapy during one time of day, and then selecting an entirely different therapy during a different time of day. Step 806 then administers the selected therapy to a patient.

By tying selection and administration of a particular therapy to specific times of day, the therapies can be automatically adjusted in a manner that more conveniently and effectively administers therapy to a patient. For example, in the DAO example, by reducing the bounce up at night, it is less likely that the therapy will provide too fast of a rate and thus keep a patient awake.

Selecting Preventative Therapy or Tiered Therapies Based on Patient State

In much the same way that preventative therapies can be selected based on the time of day, such therapies can be selected and administered based on the patient's state. Consider again the DAO example. By determining a patient's state throughout the day (i.e. active versus inactive), therapy can be adjusted to more closely conform to the patient's own lifestyle. In the case of DAO, when a patient is determined to be in an inactive state that leads to a sleep state, the bounce up can be reduced so as not to keep the patient awake. When the patient wakes up in the morning, the bounce up can be increased to a more aggressive amount.

Figure 9:
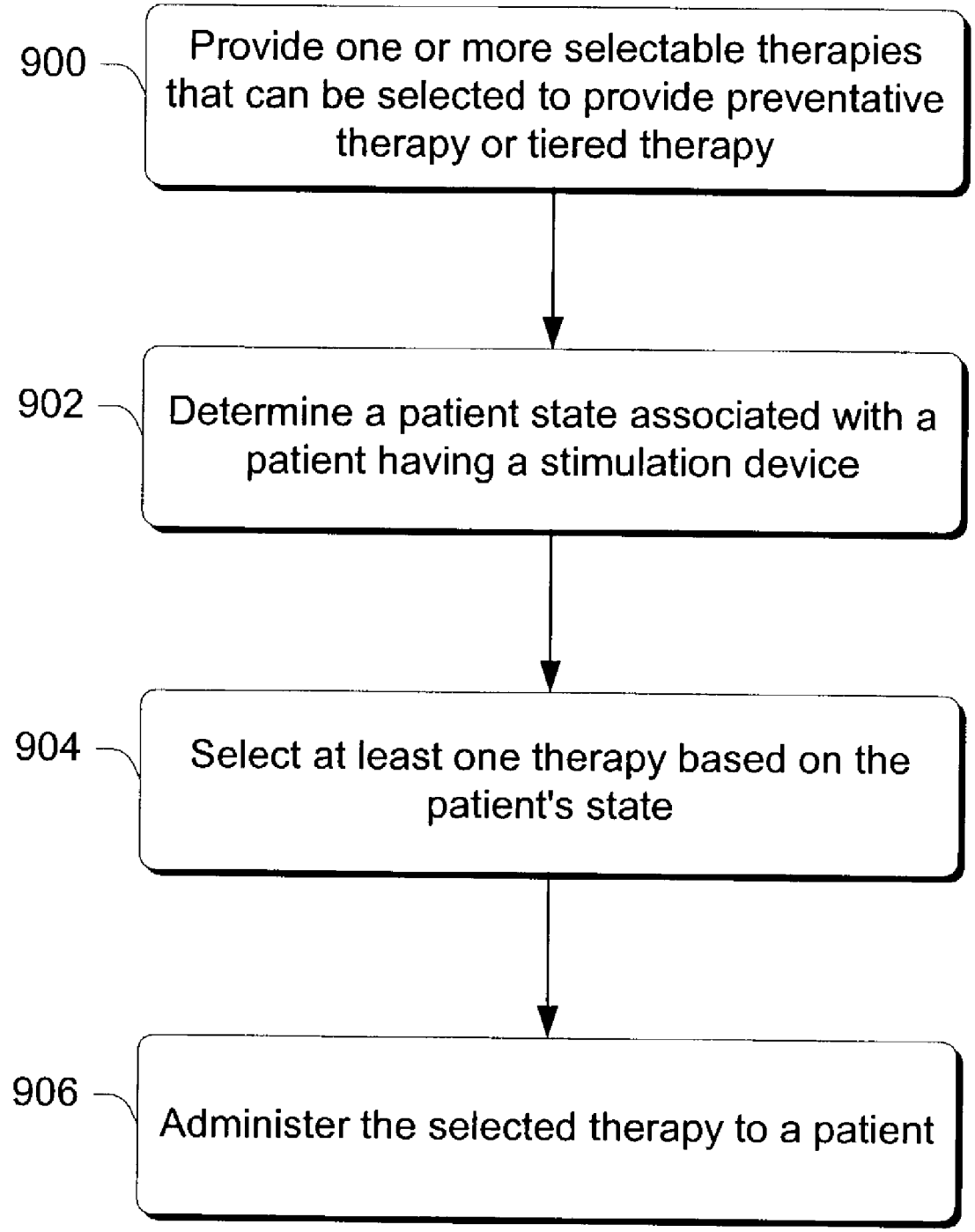
FIG. 9 is a flow diagram that describes steps in a method in accordance with one embodiment.

FIG. 9 shows an exemplary flow diagram that describes steps in a therapy method in accordance with one described embodiment. The method can be implemented in connection with any suitably configured stimulation device. One specific and non-limiting example of a stimulation device was given above.

Step 900 provides one or more selectable therapies that can be selected to provide preventative therapy or tiered therapy. Any suitable therapies can be provided and are typically provided by programming the stimulation device to provide such therapies. Step 902 determines a state associated with a patient having a stimulation device. This step can be implemented in any suitable way. Exemplary ways of determining a patients state are given above. For example, the stimulation device can use a histogram or any other suitable methods or techniques for determining the patient's state. Step 904 selects at least one preventative therapy based on the patient's state. In the example above, this step is implemented by adjusting a parameter associated with a particular selected therapy-DAO. This step can also be implemented by selecting one therapy for one patient state, and then selecting an entirely different therapy for a different patient state. Step 906 then administers the selected therapy to a patient.

Selecting Treatment Therapies Based on Time of Day

Treatment therapies, as contrasted with preventative therapies, can be considered as those therapies that are utilized to treat a particular perceived patient condition. In this embodiment, it may be more advantageous to treat a patient with certain therapies or to make adjustments to the therapies depending on the time of day.

Consider, for example, atrial fibrillation versus flutter. Atrial fibrillation is different from flutter in that in atrial fibrillation, the heart rate fluctuates between fast and slow rates (e.g. between 140 bpm and 70 bpm). In flutter, the heart beats an at an elevated and often times uncomfortable rate (e.g. 110–120 bpm). Assume that the patient is asleep at night and that an atrial fibrillation condition is detected. Assume also that there is a 10% chance that ATP therapy will successfully treat the atrial fibrillation. In this instance, it may be desirable to attempt ATP therapy two or three times to attempt to treat the atrial fibrillation. If this is unsuccessful and it is still night time, it may be more advantageous to treat the atrial fibrillation more aggressively as by administering a shock to the heart, as set forth above. Assume now that instead of an atrial fibrillation condition, a flutter condition is detected. If it is nighttime, it may be more advantageous to treat the flutter more times using ATP because there may be an 80% chance that the ATP will eliminate the flutter.

Figure 10:
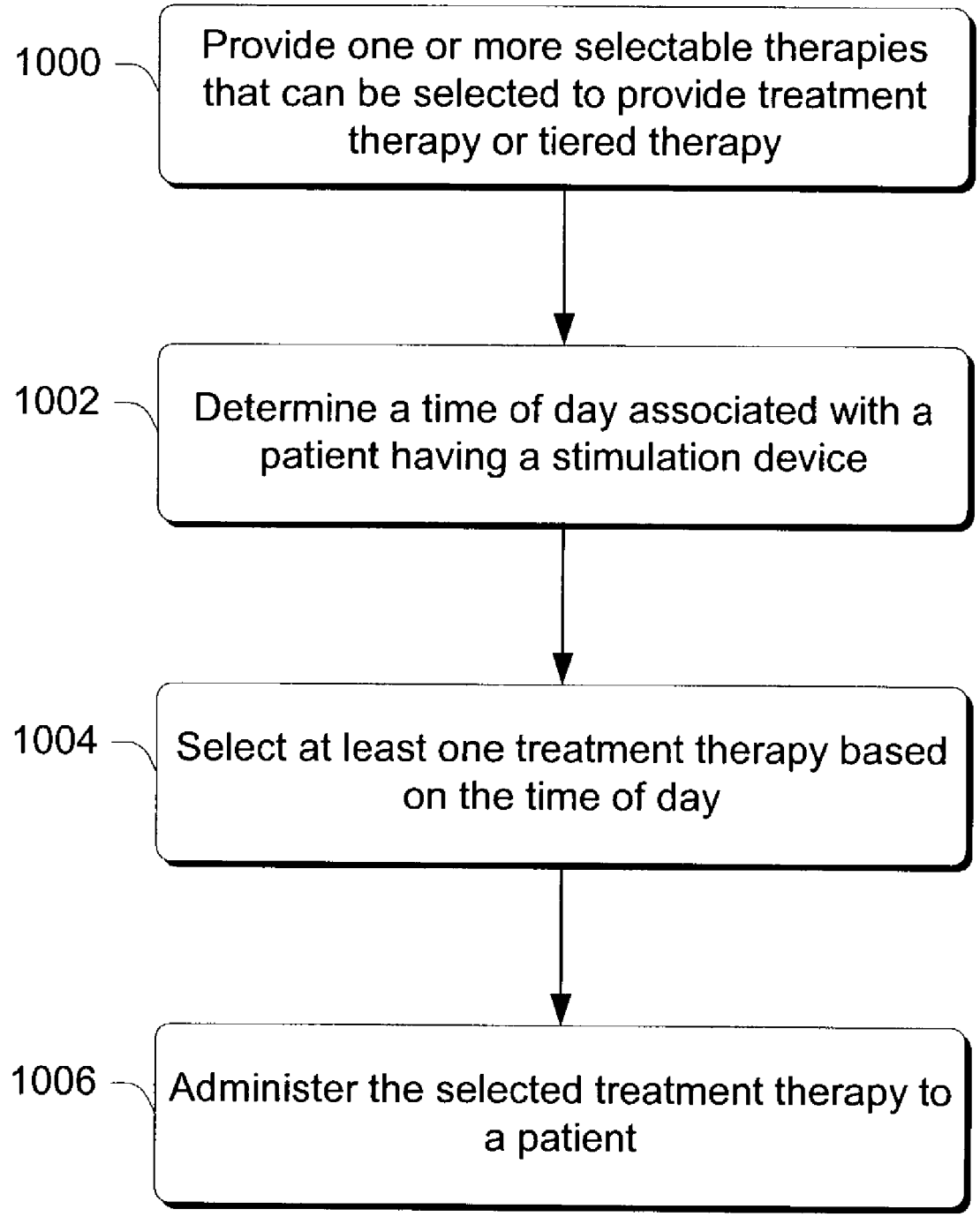
FIG. 10 is a flow diagram that describes steps in a method in accordance with one embodiment.

FIG. 10 shows an exemplary flow diagram that describes steps in a therapy method in accordance with one described embodiment. The method can be implemented in connection with any suitably configured stimulation device. One specific and non-limiting example of a stimulation device was given above.

Step 1000 provides one or more selectable treatment therapies that can be selected to provide treatment therapy or tiered therapy for a condition that has been detected in a patient. Any suitable treatment therapies can be provided and are typically provided by programming the stimulation device to provide such therapies. Step 1002 determines a time of day associated with a patient having a stimulation device. This step can be implemented in any suitable way. For example, the stimulation device can have an internal clock that it uses to ascertain the time of day. Step 1004 selects at least one treatment therapy based on the time of day. In the above example, this step was implemented by first selecting ATP and then selecting a more aggressive therapy. Step 1006 then administers the selected therapy or therapies to a patient.

By tying selection and administration of a particular treatment therapy to specific times of day, the treatment therapies can be automatically adjusted in a manner that more conveniently and effectively administers treatment therapy to a patient.

Selecting Treatment Therapies Based on Patient State

In much the same way that treatment therapies can be selected based on the time of day, such therapies can be selected and administered based on the patient's state. Consider again the ATP example and a flutter versus atrial fibrillation condition. By determining that a patient's state through the day (i.e. active versus sleeping), therapy can be adjusted to more closely conform to the patient's own lifestyle. In the above example, if a patient is determined to be in a sleep state and has a flutter condition, then it may be more advantageous to attempt ATP many times before more aggressively treating the patient. If the patient is asleep and is experiencing atrial fibrillation, then it may be more advantageous to treat the patient with ATP only a couple of times before more aggressively treating the atrial fibrillation.

Figure 11:
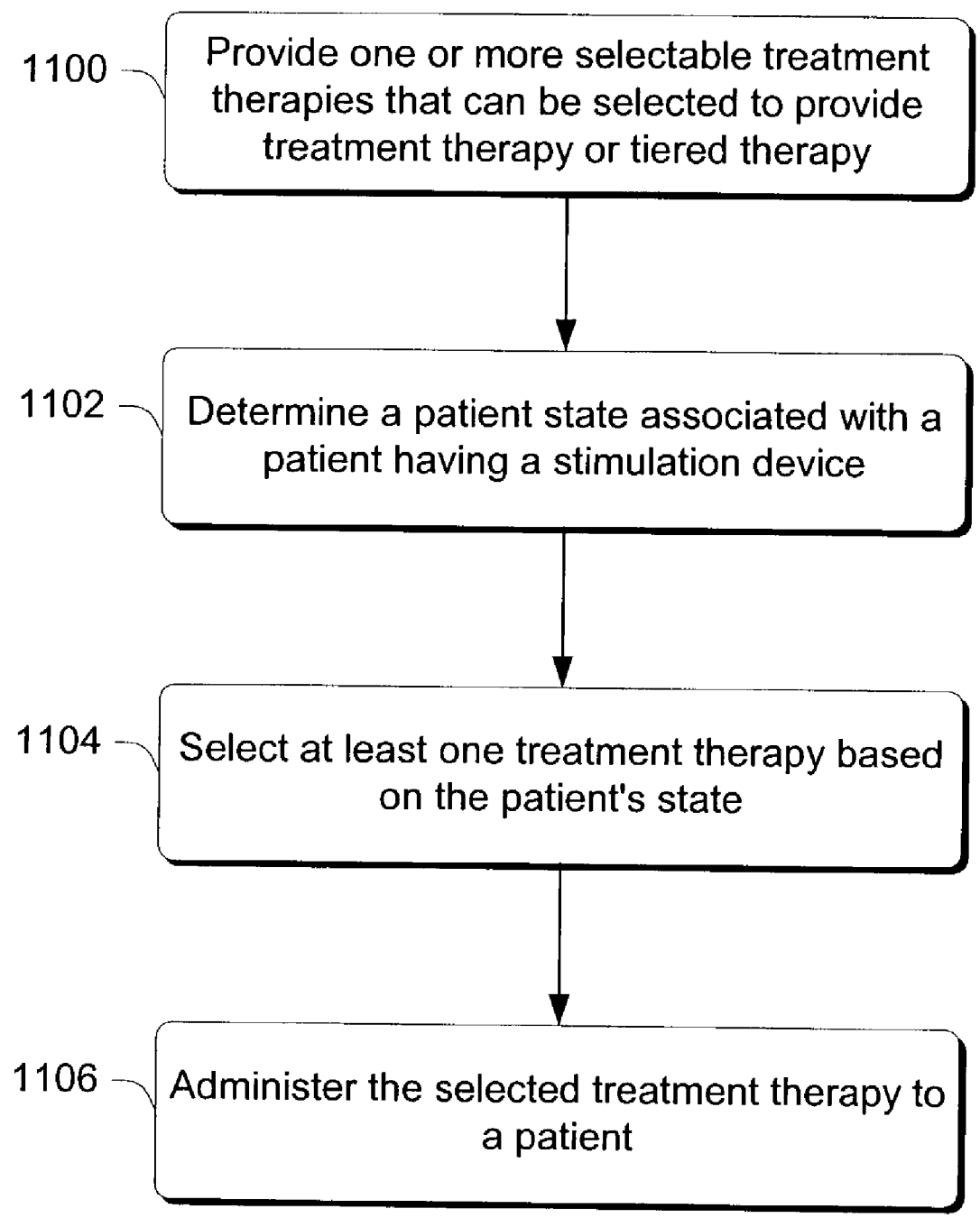
FIG. 11 is a flow diagram that describes steps in a method in accordance with one embodiment.

FIG. 11 shows an exemplary flow diagram that describes steps in a therapy method in accordance with one described embodiment. The method can be implemented in connection with any suitably configured stimulation device. One specific and non-limiting example of a stimulation device was given above.

Step 1100 provides one or more selectable treatment therapies that can be selected to provide treatment therapy or tiered therapy. Any suitable therapies can be provided and are typically provided by programming the stimulation device to provide such therapies. Step 1102 determines a state associated with a patient having a stimulation device. This step can be implemented in any suitable way. Exemplary ways of determining a patients state are given above. For example, the stimulation device can use a histogram or any other suitable methods or techniques for determining the patient's state. Assuming that a patient has a detected condition that needs treatment, step 1104 selects at least one treatment therapy based on the patient's state. In the example above, this step is implemented by first treating a patient with ATP a number of times (associated with the detected condition), and then proceeding to a more aggressive form of therapy. Step 1106 then administers the selected treatment therapy to a patient.

CONCLUSION

The embodiments described above advantageously advance the state of cardiac therapy administration. For those embodiments directed to atrial tachyarrhythmia therapy, such therapy can now be delivered with more precision, certainty, and regard to the comfort and safety of the heart patient. Other embodiments provide a robust collection of flexible and dynamic treatment regimes that enable therapy to be specifically and accurately tailored to patient states, times of day and the like. Other advantages will be apparent to those of skill in the art.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

The invention claimed is:

1. A method of administering preventative therapy comprising:
   providing one or more selectable therapies that can be selected by a stimulation device to provide a patient with preventative arrhythmia therapy;
   determining a patient state associated with the patient;
   selecting at least one preventative arrhythmia therapy based on the patient's state; and
   administering the selected at least one preventative arrhythmia therapy to the patient;
   wherein said determining comprises using a patient-specific histogram, based on one or more physiological parameters, to characterize the patient's state; and wherein said determining further comprises using a patient-specific histogram, based on one or more non-physiological parameters, to characterize the patient's state.

2. The method of claim 1, wherein said physiological parameters is based on a parameter selected from a group of parameters comprising: a QT-interval parameter, a ventricular gradient parameter, a tidal volume parameter, a minute ventilation parameter, a respiration rate parameter, an intrinsic heart rate parameter, an oxygen saturation parameter, and a pace depolarization parameter.

3. A programmable stimulation device capable of carrying out the method of claim 1.

4. A method of administering preventative therapy comprising:
providing one or more selectable therapies that can be selected by a stimulation device to provide a patient with preventative arrhythmia therapy;
determining a patient state associated with the patient;
selecting at least one preventative arrhythmia therapy based on the patient's state; and
administering the selected at least one preventative arrhythmia therapy to the patient;
wherein said determining comprises using a patient-specific histogram, based on one or more physiological parameters, to characterize the patient's state; and
wherein said determining further comprises using a patient-specific histogram, based on the patients activity, to characterize the patient's state.

5. A method of administering preventative therapy comprising:
providing one or more selectable therapies that can be selected by a stimulation device to provide a patient with preventative arrhythmia therapy;
determining a patient state associated with the patient;
selecting at least one preventative arrhythmia therapy based on the patient's state; and
administering the selected at least one preventative arrhythmia therapy to the patient;
wherein said determining comprises using a patient-specific histogram, based on one or more physiological parameters, to characterize the patient's state; and
wherein the preventative therapy prevents atrial fibrillation.

6. A system comprising:
means for providing one or more selectable therapies that can be selected by a simulation device to provide a patient with preventative arrhythmia therapy;
means for determining a patient state associated with the patient;
means for selecting at least one preventative arrhythmia therapy based on the patient's state; and
means for administering the selected at least one preventative arrhythmia therapy to the patient;
wherein said means for determining comprises using a patient-specific histogram, based on one or more physiological parameters, to characterize the patient's state; and
wherein said means for determining further comprises using a patient-specific histogram, based on one or more non-physiological parameters, to characterize the patient's state.

7. A system comprising:
means for providing one or more selectable therapies that can be selected by a stimulation device to provide a patient with preventative arrhythmia therapy;
means for determining a patient state associated with the patient;
means for selecting at least one preventative arrhythmia therapy based on the patient's state; and
means for administering the selected at least one preventative arrhythmia therapy to the patient;
wherein said means for determining comprises using a patient-specific histogram, based on one or more physiological parameters, to characterize the patient's state; and
wherein the preventative arrhythmia therapy prevents atrial fibrillation.

8. The system of claim 7, wherein said physiological parameters is based on a parameter selected from a group of parameters comprising: a QT-interval parameter, a ventricular gradient parameter, a tidal volume parameter, a minute ventilation parameter, a respiration rate parameter, an intrinsic heart rate parameter, an oxygen saturation parameter, and a pace depolarization parameter.

9. A system comprising:
means for providing one or more selectable therapies that can be selected by a stimulation device to provide a patient with preventative arrhythmia therapy;
means for determining a patient state associated with the patient;
means for selecting at least one preventative arrhythmia therapy based on the patient's state; and
means for administering the selected at least one preventative arrhythmia therapy to the patient;
wherein said means for determining comprises using a patient-specific histogram, based on one or more physiological parameters, to characterize the patient's state; and
wherein said means for determining further comprises using a patient-specific histogram, based on the patient's activity, to characterize the patient's state.

* * * * *